United States Patent [19]

Wong

[11] Patent Number: 5,047,639

[45] Date of Patent: Sep. 10, 1991

[54] CONCENTRATION DETECTOR

[76] Inventor: Jacob Y. Wong, 4589 Camino Molinero, Santa Barbara, Calif. 93110

[21] Appl. No.: 455,072

[22] Filed: Dec. 22, 1989

[51] Int. Cl.$^5$ .......................... G01N 21/39; G01J 3/00
[52] U.S. Cl. ..................................... 250/341; 250/343; 250/354.1; 356/318; 356/436
[58] Field of Search ............ 250/341, 343, 339, 354.1; 372/18, 20, 32; 356/436, 437, 318

[56] References Cited

U.S. PATENT DOCUMENTS

| | | | |
|---|---|---|---|
| 3,995,960 | 12/1976 | Fletcher et al. | 356/204 |
| 4,068,125 | 1/1978 | Bell | 250/340 |
| 4,084,906 | 4/1978 | Bibbero | 356/96 |
| 4,410,273 | 10/1983 | Mantz et al. | 356/319 |
| 4,557,603 | 12/1985 | Oehler et al. | 356/418 |
| 4,684,258 | 8/1987 | Webster | 356/409 |
| 4,684,805 | 8/1987 | Shu-Ti Lee et al. | 250/343 |
| 4,748,632 | 5/1988 | Preston | 372/32 |
| 4,780,613 | 10/1988 | Berstein et al. | 250/343 |
| 4,883,963 | 11/1989 | Kemeny et al. | 250/339 |
| 4,934,816 | 6/1990 | Silver et al. | 356/409 |

OTHER PUBLICATIONS

Tsuchida, et al., "Frequency Stabilization of AlGaAs Semiconducter Laser to the Absorption Line of Water Vapor", Japanese Jour. of Applied Physics, vol. 21, No. 1, 1982, pp. L1-L3.
Sollberger, et al., "Frequency Stabilization of Semiconductor Lasers for Applications in Coherent Communication Systems", Journal Lightwave Tech., vol. Lt-5, No. 4, 1987, pp. 485-491.
Wenke, et al., "Characteristics of a Compact Three Cavity Laser Configuration", Journal of Lightwave Tech., vol. LT-5, No. 4, 1987, pp. 608-615.
Raab, et al., "Application of a Diode Laser with an External Resonator in High Resolution Spectroscopy", Sov. J. Quantum Electron, 11(8), 1981, pp. 1068-1071.
Yabuzaki, et al., "Frequency Locking of a GaAlAs Laser to a Doppler-free Spectrum of the Cs-D2 Line", Japanese Jour. of Applied Physics, vol. 20, No. 6, 1981, pp. L451-L454.

Primary Examiner—Constantine Hannaher
Assistant Examiner—Edward J. Glick
Attorney, Agent, or Firm—John A. Frazzini

[57] ABSTRACT

A concentration detector having a light source that is responsive to a chemical absorption peak to produce substantially monochromatic light at a wavelength of this absorption peak. The wavelength can be stabilized against an absorption peak in a reference chemical or by an absorption peak in a sample being measured in the concentration detector.

5 Claims, 5 Drawing Sheets

CONCENTRATION DETECTOR

BACKGROUND OF THE INVENTION

This invention relates in general to concentration detectors and relates more particularly to a single mode diode laser that produces light at a wavelength λ that is selected with sufficient accuracy and stability to be suitable for use in spectrometry.

Oxygen concentration sensors are useful in hospitals to monitor the concentration of oxygen in prenatal care and in other environments in which the oxygen concentration is critical. Oxygen can be poisonous if supplied in too high a concentration, so it is important that the oxygen concentration be neither too high nor too low. At the present time, an oxygen sensor is available that measures the oxygen concentration by means of an oxygen-reduction reaction. The oxygen oxidizes an electrode of an electrochemical cell, thereby releasing electrons that produce a current level proportional to the concentration of the oxygen. Unfortunately, this measurement can take on the order of a half minute and therefore is much slower than would be desired. Therefore, it would be advantageous to have an oxygen sensor that measures the oxygen concentration in a much shorter period.

Sample concentrations are also measured in the field of spectrometry. In spectrophotometry, light is passed through a sample to a detector and the spectral distribution of absorption is measured. The concentration of a particular substance in a sample under test is measured by measuring the height of a spectral peak located at a peak in the absorbance spectrum of that substance.

Soon after lasers were first developed it was appreciated that lasers are particularly suitable for use in spectroscopy because they produce extremely narrow light beams having an extremely high energy density. This enables a high concentration of light to be passed through a very small sample, thereby enabling spectroscopic measurements to be performed on microliter sized samples. A laser beam can also be very monochromatic, as is needed for high resolution spectroscopic measurements.

Unfortunately, most lasers cannot be tuned over a significant spectral range so that such lasers cannot be used for detecting a wide range of substances. Although dye lasers, certain solid state lasers (such as $Al_2O_3:Ti^{3+}$ solid state lasers) and semiconductor lasers can be tuned over a useful range of wavelengths, most other lasers are used as light sources only at a discrete wavelength. This discrete wavelength is determined by the energy band structure of the lasing medium and does not typically coincide with the wavelength of interest in detecting most substances. Therefore, most spectroscopic and spectrometric systems utilize tunable lasers.

Of the three above-mentioned tunable lasers, semiconductor lasers (also referred to as diode lasers) are the most attractive for commercial spectrometers because of their simplicity of operation (i.e., they are pn junctions), their small size, their wide range of tunability and their relatively low cost. In general, diode lasers can be tuned by variation of drive current through the diode and by variation of the diode temperature. Another factor making diode lasers attractive for spectrometry is that, over the past two decades, a great amount of research has been directed to producing inexpensive, dependable, single mode diode lasers.

Most of this research has been motivated by telecommunication applications in which single mode lasers are needed to produce a carrier for transmission through optical fibers. In such applications, it is important that this monochromatic light beam carry light of a wavelength that is not strongly attenuated by the optical fibers. This has resulted in the selection of a few standard wavelengths for use in telecommunications and this in turn has directed much of the research to the improvement of devices that operate at these standard wavelengths.

AlGaAs diode lasers at around 820 nm and InGaAsP diode lasers at 1.30 μm and 1.55 μm received a substantial amount of research efforts because they take advantage of the optical fiber absorption minima at these wavelengths. These diodes exhibit excellent operational characteristics, including high monochromaticity (0.01-0.1 Å FWHM), low threshold current (typically on the order of tens of milliamps), excellent output power, excellent frequency stability, high modulation rate (up to 3 GHz) of the drive current and long life (greater than 100,000 hours cw) while operating at up to 50° C. Unfortunately, since this research was directed to telecommunications applications, much of this work is not necessarily of use in spectrometry.

Lasers are optical oscillators that can potentially produce light at any of the resonant wavelengths of the optical cavity modes. Since the gain spectrum of a laser is typically much wider than the wavelength spacing between cavity modes, more than one mode can experience a net gain of at least unity. Each of such net gain modes will then grow until it saturates. Lasers can therefore operate in three different modes of operation: modelocked, multimode and single mode.

In modelocked operation (also referred to as phase-locked operation), only two modes are allowed to lase and are phaselocked so that the output intensity of these two interfering signals exhibits a sinusoidal modulation at the difference frequency of these two lasing modes. In multimode operation, at least two cavity modes are allowed to lase, but the relative phase between each mode varies incoherently so that the output signal does not exhibit modulation at the difference frequencies. In single mode operation, the laser is configured to allow only a single mode to lase. This is achieved by damping all but one of the modes of the laser cavity that would otherwise exhibit a net gain greater than one.

There are two widely used methods of damping unwanted modes: coupled cavity and distributed feedback (DFB). In a DFB type single mode laser, the thickness of one of the layers of the laser is varied spatially at a period equal to the wavelength of the single mode that is to be selected for lasing. The resulting periodic perturbation of the refractive index provides mode selective feedback by means of backward Bragg scattering. Unfortunately, the period of variation of layer thickness is fixed at the time of manufacture so that this type of laser cannot be tuned to an absorption peak in the substance to be detected. Also, the manufacturing process does not produce a period of thickness variation with sufficient repeatability to make these lasers suitable for use in spectrometry. A very limited amount of tuning can be produced by variation of the drive current and/or the temperature of the diode laser, but a very elaborate temperature control system would be required to select a wavelength within the few tenths of an Angstrom accuracy needed for gas spectrometry. This would require control of the temperature to an accuracy of less than 0.05° C.

In a coupled cavity type single mode laser, an external cavity provides the wavelength dependent feedback needed for single mode operation. This external cavity can be either pumped or unpumped. When the external cavity is pumped, this introduces an additional degree of freedom that can be used to control the behavior of the laser. This external cavity introduces damping that varies periodically with wavelength. The mode selected for single mode operation is the mode having the greatest net gain and is typically the mode having the lowest cavity loss closest to the peak of the laser gain profile.

These two types of single mode diode lasers exhibit superior performance for many applications, but the cost and complexity of their operation are justified only in applications, such as telecommunications, where the benefits justify the increased cost. Of greater importance to spectrometric applications, these single mode lasers generally have limited tunability. Because of the narrowness of the absorption peaks in spectrometry, suitable optical sources should not only provide tunability, but should also provide the accuracy and stability of wavelength selection needed to select a laser wavelength that accurately matches the wavelength needed for sample measurement. The telecommunication application toward which most prior work was directed does not require such accurate, stable wavelength selection.

SUMMARY OF THE INVENTION

For high sensitivity spectrometric measurement of gas concentrations, the spectrometer light source should provide radiation that exhibits a spectral distribution in which substantially all of the radiant energy is contained within a single narrow peak centered at an absorption peak of the substance to be measured. Preferably, the radiation peak should have a half-width comparable to or smaller than the half-width of the absorption peak of the substance under test because, if the radiation peak is much wider than this absorption peak, then the radiation peak could overlap absorption peaks of other substances and produce spurious results. However, since the absorption peaks can be quite narrow, it is not a simple task to produce a narrow radiation peak that coincides with the selected absorption peak.

In accordance with the preferred embodiments, a simple, reliable, low cost monochromatic laser is presented that has a stable, accurately selected wavelength $\lambda$ suitable for measuring gas concentrations by an optical absorption technique. This laser source operates in a spectral region in which the gas to be measured exhibits several very narrow (on the order of 0.01 Å wide) spectral lines. This laser produces a spectral distribution having a single peak of width comparable to the linewidth of the spectral lines in the gas being detected. The wavelength $\lambda$ of this single peak is controlled to be coincident with one of the spectral peaks in the gas being detected.

This laser takes advantage of the very small linewidth (on the order of 0.01 Å FWHM for peaks in the near infrared region for a gas at Standard Temperature and Pressure) of a vibration-rotational sharp line of an absorption spectrum of a gas. This laser also takes advantage of the fact that the full width half maximum (FWHM) of an emission line of a single mode diode laser is also of the same order of magnitude. Because of this almost perfect spectral match, it is possible to stabilize the emission wavelength $\lambda$ of a diode laser to an accuracy of the same order (i.e., 0.01 Å or less) by a simple feedback scheme.

The laser beam from the diode laser is passed through a gaseous sample containing a reference gas component. The laser beam is incident on a detector that produces a signal having a minimum whenever the laser's wavelength coincides with one of the absorption peaks of the reference gas. The wavelength of the laser is controlled by control of the temperature of the diode laser and by control of the drive current to the diode laser.

In the preferred embodiment, the temperature of the diode laser is set to a fixed value and the drive current through the laser is initially set to a value that is known to produce a laser beam wavelength that is near an absorption peak of the reference gas component. A feedback loop then varies the drive current until the wavelength is centered on an absorption peak of the reference gas component.

An alternate embodiment is suitable for use in measuring the concentration of a plurality of gases. In this embodiment, the laser beam is divided into a reference beam that is passed through a reference cell containing the reference gas component and into a sample beam that is passed through the gaseous sample. The reference beam is incident on a detector that produces a signal that is used in a feedback loop to center the wavelength of the diode laser onto an absorption peak of the reference gas. The sample beam is incident on another detector that produces a signal that is used to measure the concentration of the reference gas component in the gaseous sample.

A feedback loop includes dithering circuitry that produces both a first harmonic component signal and a second harmonic component signal. The first harmonic component signal is used to lock the laser wavelength to the center wavelength of an absorption peak of the reference gas. The second harmonic component signal indicates the concentration of the reference gas within the gaseous sample. The second harmonic component signal also indicates whether the laser wavelength lies within an absorption peak. At device turn-on, a ramp signal sweeps the wavelength until the second harmonic signal indicates that the laser wavelength lies within an absorption peak.

These and other objectives and advantages of the present invention will become clear from the detailed description given below in which a preferred embodiment is described in relation to the drawings. The detailed description is presented to illustrate the present invention, but is not intended to limit it.

DESCRIPTION OF THE FIGURES

In the figures, the first digit of a reference numeral indicates the first figure in which is presented the element indicated by that reference numeral.

DESCRIPTION OF THE PREFERRED EMBODIMENT

Figure 1:
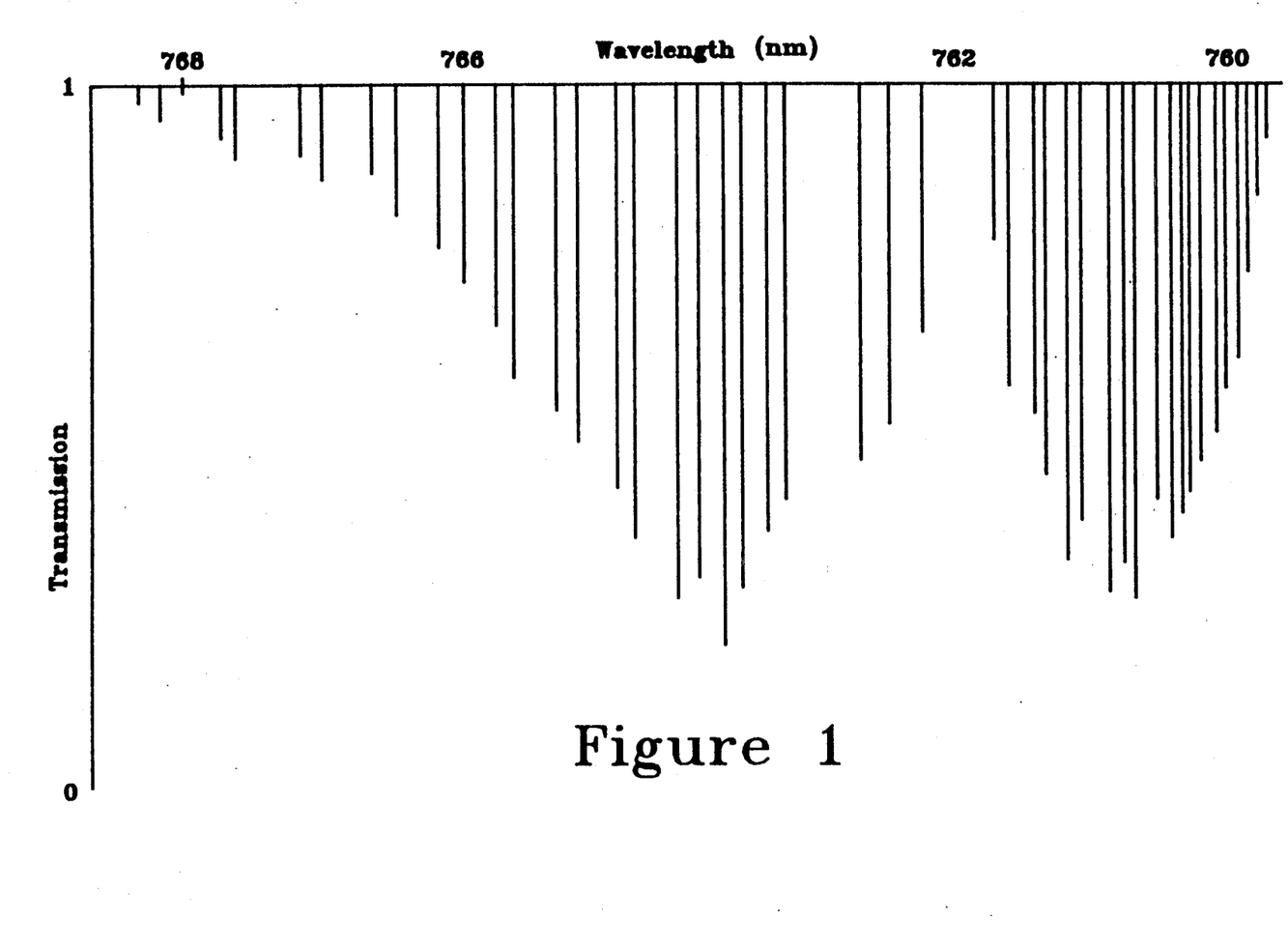
FIG. 1 shows the A-band vibration-rotational spectrum of molecular oxygen in the near infrared showing the sharp line features at Standard Temperature and Pressure.
Figure 2:
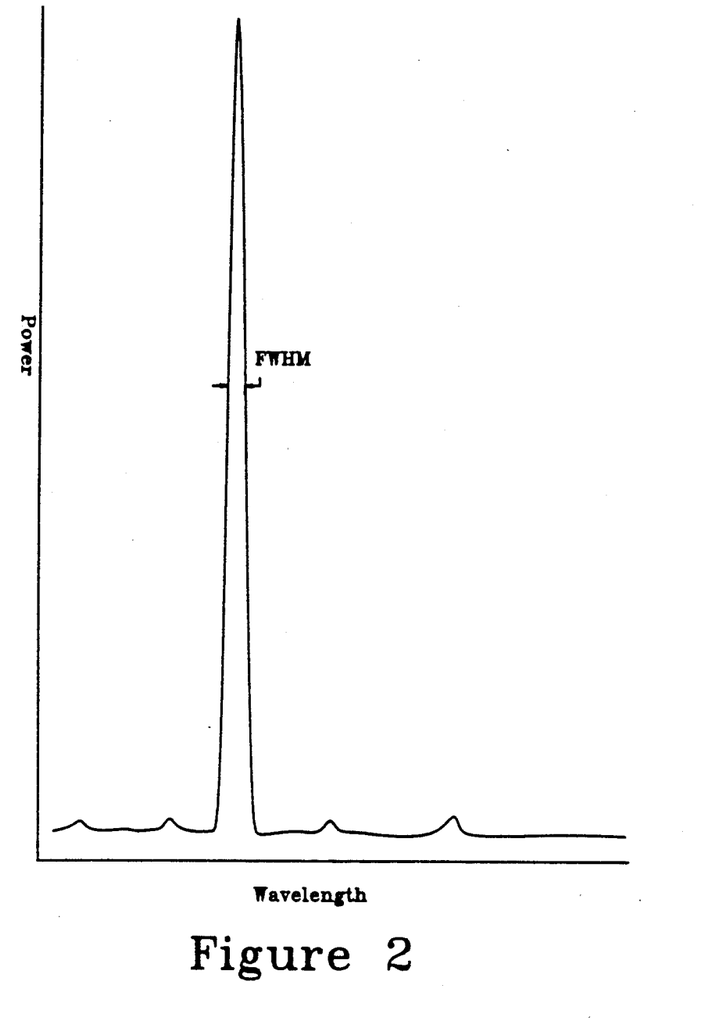
FIG. 2 shows the narrow spectral width of emission peaks in a typical spectral emission output of a diode laser operating single mode at Standard Temperature and Pressure.

FIG. 1 shows the A-band vibration-rotational absorption spectrum of molecular oxygen in the near infrared at Standard Temperature and Pressure. The absorption lines in this spectrum exhibit a linewidth (FWHM) on the order of 0.01–0.1 Å. Many other gases exhibit similar spectra and linewidths. A typical spectral emission output of a diode laser operating single mode at Standard Temperature and Pressure is presented in FIG. 2. The linewidth of the central peak is also on the order of 0.01–0.1 Å. The other peaks are much smaller than the central peak so that the laser output is substantially monochromatic. When this peak is centered on an absorption peak of a chemical gas component, substantially all of the laser beam light intensity is utilized in detection of the chemical gas component, thereby optimizing the use of the laser light.

Figure 4:
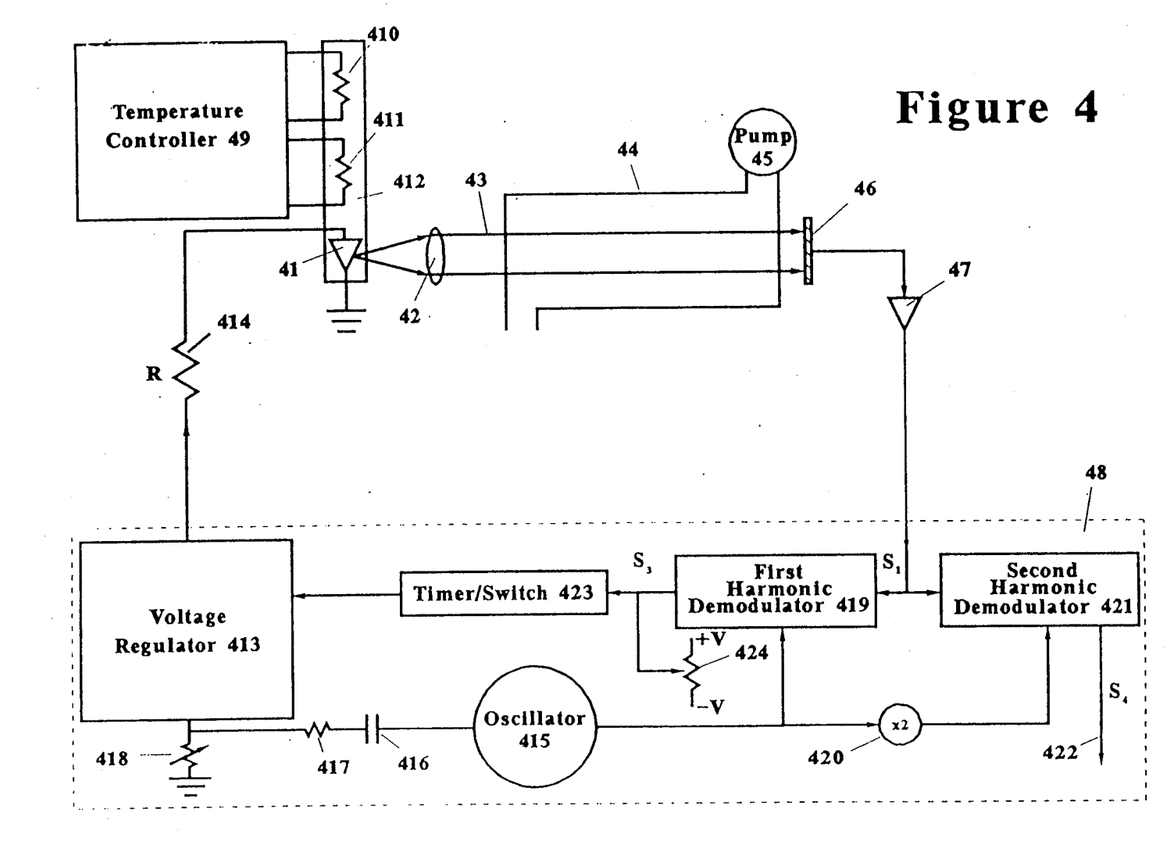
FIG. 4 is a block diagram of the preferred embodiment of a laser suitable for use in gas spectroscopy.

FIG. 4 is a block diagram of the preferred embodiment of a gas concentration detector that utilizes a laser having feedback control to lock the wavelength of the laser to an absorption peak of a chemical component of a gaseous sample, thereby optimizing sensitivity. In this gas concentration detector, a laser diode 41 produces light that is focussed by a lens 42 into a beam 43 that passes through a sample gas within a sample chamber 44. A pump 45 draws the sample gas through this chamber. Beam 43 is incident on a photodetector 46 that produces an output signal to a buffered amplifier 47. A feedback section 48 is responsive to an output signal $S_1$ from amplifier 47 to center the wavelength of beam 43 onto an absorption peak of the chemical component of the sample gas.

A temperature controller 49, coupled to a thermistor 410 and a heater element 411, maintains the temperature of a diode housing 412 at 40° C.±0.5° C. During the manufacture of the gas concentration detector, diode laser 41 is tested to determine what drive current is needed, for diode laser operation at 40° C., to produce a wavelength that is centered on a selected absorption peak of the chemical component to be measured. A voltage regulator 413 controls the amount of drive current provided to diode 41 through an input resistor 414. At instrument turn-on, this drive current is substantially in the middle of the range of drive current range. The input resistor 414 is adjusted at the factory to set the initial drive current to a value that produces an initial wavelength that is within about 0.2 nm of an absorption peak. It is not necessary that the wavelength coincide with any particular one of the absorption peaks, but, for optimum sensitivity, the particular peak for which coincidence is achieved should be one of the larger peaks. As FIG. 1 illustrates, if the wavelength is set within about 1 nm of 764.8 nm or within about 0.5 nm of 760.4 nm, then the laser will lock onto one of the largest peaks.

Figure 3:
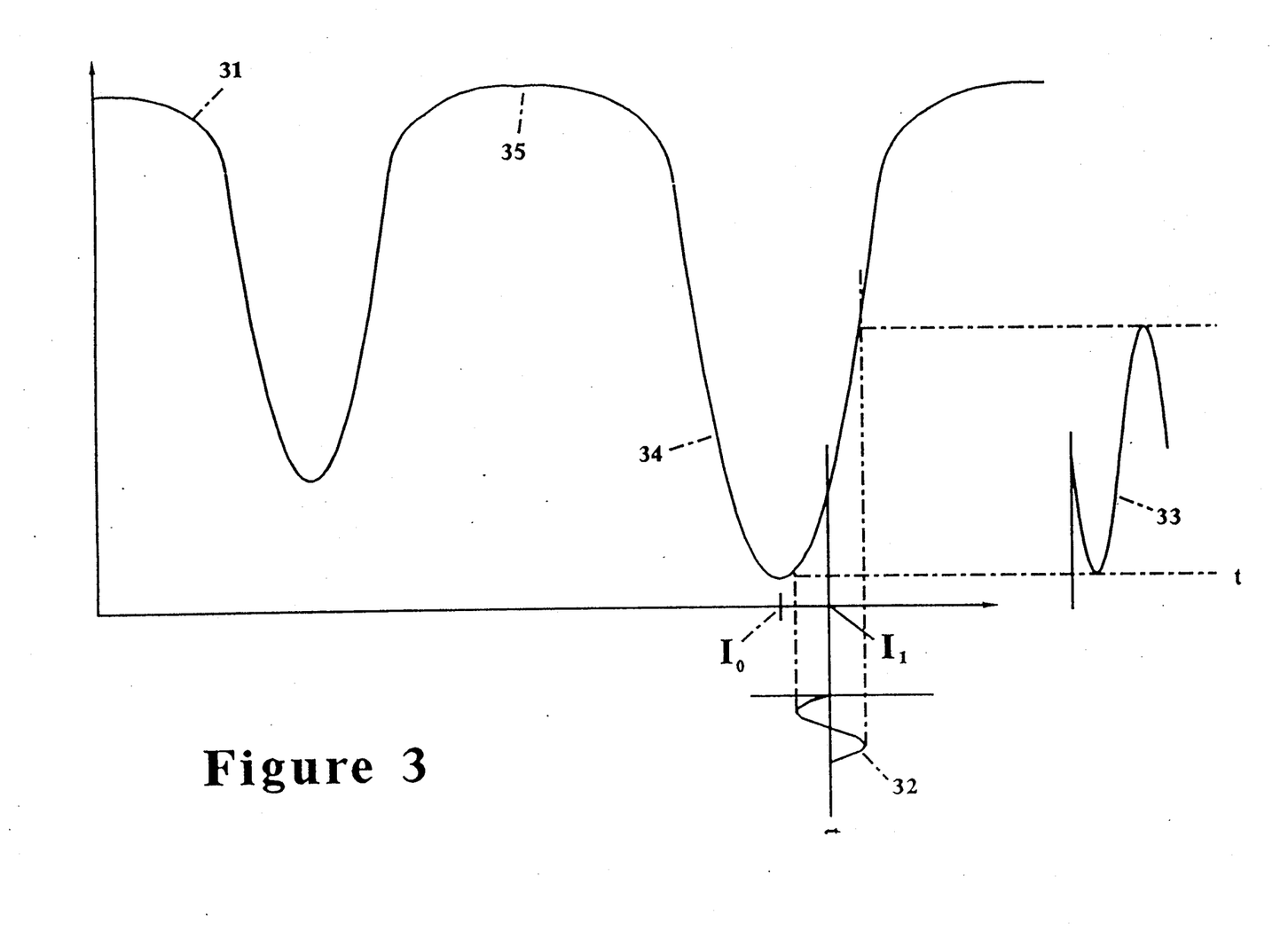
FIG. 3 illustrates how dithering enables the diode laser wavelength to be locked to the wavelength of an absorption peak of the reference gas.

Feedback section 48 includes dithering circuitry 413, 415–424 that locks the diode laser wavelength to the center wavelength of an absorption peak of the chemical gas component to be measured. The operation of the dithering circuitry can be understood by reference to FIG. 3. Curve 31 is a plot of the output signal $S_1$ from buffered amplifier 47 as a function of drive current I. If the drive current varies with time as $I_1 + I_s \cdot \sin(2\pi ft)$ (as shown by curve 32), then $S_1$ has the temporal variation shown by curve 33. This response can be evaluated mathematically near the absorption peak 34 at drive current $I = I_0$ by making a second order Taylor expansion of the absorption peak: $P \sim P_0 + P_2 \cdot (I - I_0)^2$ where $P_0$ and $P_2$ are the Taylor series zeroth and second order coefficients, respectively. Therefore $$P \sim P_0 + P_2 \cdot [I_1 - I_0 + I_m \cdot \sin(2\pi ft)]^2 = [P_0 + P_2 \cdot (I_1 - I_0)^2] + 2P_2 \cdot (I_1 - I_0) \cdot I_m \cdot \sin(2\pi ft) + P_2 \cdot I_m^2 \cdot \sin^2(2\pi ft) \quad (1)$$

which can be rewritten as $$P \sim A + B \cdot \sin(2\pi ft) + C \cdot \sin^2(2\pi ft) = A + B \cdot \sin(2\pi ft) + C \cdot (\tfrac{1}{2}) \cdot [1 - \cos(4\pi ft)] \quad (2)$$

The coefficient B is proportional to $I_1 - I_0$ and therefore indicates how far the drive current I is from the current $I_0$ at which the laser beam wavelength would be centered on the absorption peak 34. The coefficient C is proportional to the curvature of peak 34 which in turn is proportional to the amplitude of that peak. Within an absorption peak, the curvature is positive so that this coefficient indicates whether the laser wavelength is within an absorption peak.

An oscillator 415 provides a sinusoidal signal of frequency f on the order of 1 kHz through a capacitor 416 that blocks dc and through a pair of resistors 417 and 418 that adjust the amplitude of sinusoidal signal provided to voltage regulator 413. Because the diode laser's wavelength is changed much more quickly in response to a change in drive current than to a change in current to heater element 411, voltage regulator 413 responds to this sinusoidal signal by adding a sinusoidal component of frequency f to the drive current. This in turn produces components of signal $S_1$ at integral multiples of frequency f.

A first harmonic demodulator 419, responsive to $S_1$ and the oscillator signal, suitably phase shifted to be in phase with the component of $S_1$ at frequency f, produces an output signal $S_3$ proportional to B which in turn is proportional to the time integral of $I_1 - I_0$. Signal $S_3$ is supplied to voltage regulator 413 which produces in the drive current I a component proportional to $S_3$. This pushes the dc component of the drive current I to $I_0$, thereby locking the diode laser wavelength to the center of absorption peak 34.

At instrument turn-on, a timer/switch 423 disconnects first harmonic demodulator 419 from voltage regulator 413 for a time interval sufficient to enable diode housing 411 to reach its operating temperature before the signal $S_3$ from first harmonic demodulator 419 is allowed to adjust the drive current. This enables the laser wavelength to reach its intended startup value before signal $S_3$ begins to adjust the wavelength to lock onto an adjacent absorption peak.

A multiplier 420 provides to a second harmonic demodulator 421 a sinusoidal output signal of frequency $2f$ that is phase shifted to be in phase with the component of signal $S_1$ of frequency $2f$. The output signal $S_4$ from second harmonic demodulator is proportional to the factor C. This factor is positive for a minimum and is negative for a maximum. In the regions (such as region 35) between the peaks, the factor C is negative and very small. Within an absorption peak, C is positive. When the laser wavelength is centered in a peak, signal $S_4$ is large and proportional to the amplitude of that peak.

Signal $S_4$ is therefore output at an output port 422. The output signal is easily calibrated by flowing through sample chamber 44 a reference quantity of known concentration of the chemical gas component. In the case of an oxygen concentration detector, this is easily achieved by flowing ambient atmosphere through the chamber since its oxygen concentration is known to be 20.6%.

Figure 5:
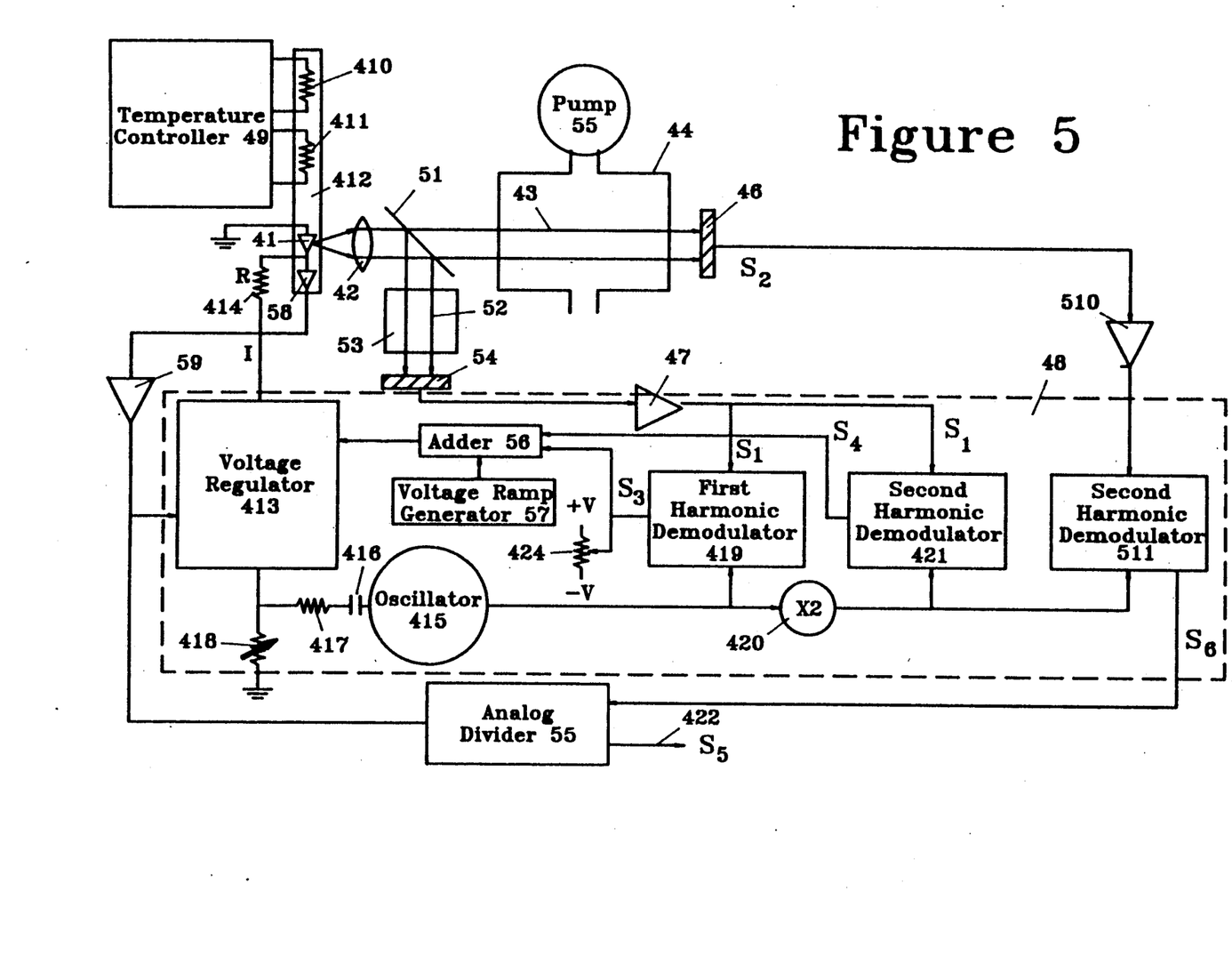
FIG. 5 is a block diagram of an alternate embodiment of a laser suitable for use in gas spectroscopy.

FIG. 5 is an alternative embodiment in which the elements that are in common with the embodiment of FIG. 4 retain the same reference numbers as in FIG. 4. The embodiment of FIG. 5 differs in the following aspects from the embodiment of FIG. 4. A beam splitter, such as a half silvered mirror 51 or an optical fiber beam splitter, splits the light passing through lens 42 into the sample beam 43 that passes through sample chamber 44 and a reference beam 52 that passes through a reference chamber 53 to a second detector 54. The signal $S_1$ provided to both the first harmonic demodulator 419 and the second harmonic demodulator 421 is now provided by detector 54 which is responsive to a beam through the reference chamber 53. A signal $S_2$, that carries information about the concentration of the chemical gas component in a sample gas, is supplied through a buffer 510 to an additional second harmonic demodulator 511. This demodulator is also responsive to the output of multiplier 420 to provide to analog divider 55 a dc signal $S_6$ proportional to the component of $S_2$ at frequency $2f$. Thus, in this embodiment, feedback circuitry 48 locks the laser wavelength to an absorption peak of the reference gas instead of to an absorption peak of the gaseous sample.

The output $S_3$ of first harmonic demodulator 419 is now provided to voltage regulator 413 via an adder 56 in which, during an initial turn-on interval, it is added to a ramp signal from a voltage ramp generator 57. As a result of this ramp signal, during the turn-on interval, the wavelength is swept until the laser wavelength overlaps an absorption peak. The occurrence of this overlap is indicated by the output signal $S_4$ of second harmonic demodulator 421 going positive. In response to this, adder 56 ceases to add the ramp voltage to the signal provided to voltage regulator 413, thereby enabling signal $S_3$ to produce lock without any interference from the ramp signal.

Many conventional diode laser packages include a photodetector 58 that is used in this embodiment to make the output signal insensitive to amplitude variations in the laser signal. The current through this photodetector is supplied through a buffer amplifier 59 to analog divider 55 where an output signal $S_5$ is produced that is proportional to the ratio of signal $S_6$ from second harmonic demodulator 511 to the signal from amplifier 59.

This embodiment has the following advantages. The absorption peak to which the wavelength is locked will generally be significantly greater than in the embodiment of FIG. 4 because the fraction of the gaseous sample that consists of the chemical gas component to be detected can be as low as a few percent, whereas the reference gas will generally be selected to consist purely of the chemical gas component to be detected. This embodiment can therefore ensure stable lock even when the gaseous sample contains only a few percent of the chemical gas component to be detected. Use of pure reference gas in the reference cell eliminates the possibility that the laser wavelength will be locked to an absorption peak of some chemical other than the chemical gas component to be detected. The reference gas can be changed so that this embodiment can be used as a concentration detector for more than one chemical gas component. However, in applications where a single gas component, such as oxygen, needs to be detected over a range that does not extend too close to zero, the embodiment of FIG. 4 is preferred because of its greater simplicity.

I claim:

1. A concentration detector comprising:
   a single chamber, only, for containment of a sample chemical, the concentration of which is to be measured;
   a first optical detector that produces a signal $S_1$ indicative of an intensity of light incident thereon;
   a tunable source of substantially monochromatic light of a wavelength $\lambda$, said substantially monochromatic light being directed through said single chamber onto said first optical detector;
   means, coupled to said first optical detector and to said tunable source of light and responsive to the measured intensity of light incident on said first optical detector, for locking the wavelength $\lambda$ to an absorption peak of said sample chemical;
   means, coupled to said first optical detector, for producing an output signal indicative of the intensity of light incident on said first optical detector;
   whereby, by use of only a single chamber for containment of a sample that is used both for adjustment of the wavelength of the light to an absorption peak of the sample and for measuring the amount of absorption of this sample, a simpler, more compact, less expensive, high sensitivity concentration detector is produced than in devices in which additional chambers or sensing means or both are included to provide these two functions of adjusting the wavelength and of measuring an amount of absorption of said light in passing through said chamber and sample.

2. A concentration detector as in claim 1 wherein said means for locking comprises:
   dithering circuitry, having an oscillator of frequency f, that introduces into the light a periodic variation of the wavelength at a frequency f;
   means, responsive to a variation in a signal $S_1$ at frequency f, for producing a signal $S_3$ proportional to said variation of signal $S_1$ at frequency f and for providing signal $S_3$ to said tunable source, said tunable source being responsive to this signal $S_3$ to adjust the wavelength $\lambda$ to an absorption peak of the chemical component.

3. A concentration detector as in claim 1 wherein said tunable source of monochromatic light is a diode laser and wherein said means for locking comprises:
   means for controlling the temperature of said tunable source of substantially monochromatic light; and
   means, responsive to $S_3$, for controlling a drive current through said tunable laser; and said concentration detector further comprises
   a timer/switch that, when said concentration detector is first turned on, disconnects said means for locking from said diode laser only for a time interval sufficient to enable the diode laser to reach a stable operating temperature before the signal $S_3$ is allowed to adjust the drive current.

4. A concentration detector as in claim 3 further comprising:

an adjustable input resistor through which said drive current passes to said tunable laser, said resistor capable of being set to a selectable resistance at which, when the diode laser reaches a stable operating temperature before said timer/switch couples said means for locking to said diode laser, the wavelength of the laser is substantially equal to the wavelength of said absorption peak, whereby the wavelength is able to be adjusted close enough to the wavelength of a preselected absorption peak that the means for locking will lock onto this preselected absorption peak instead of some other peak past which it might be passing as the temperature is initially adjusted after instrument turn-on.

5. A concentration detector as in claim 1 further comprising:
   a second optical detector, upon which light is directly incident from said tunable source of monochromatic light without passing first through said chamber, that produces a reference signal proportional to the intensity of light incident thereon; and
   means, responsive to output signals from said first and second optical detectors, for producing a corrected output signal proportional to the ratio of the intensity of light incident on the first detector to the intensity of light incident on the second detector, whereby variations in the intensity of this emitted light does not show up as spurious concentration values.

* * * * *